United States Patent
Druzgala

(10) Patent No.: US 6,809,116 B2
(45) Date of Patent: Oct. 26, 2004

(54) MATERIALS AND METHODS FOR THE TREATMENT OF DEPRESSION

(75) Inventor: Pascal Druzgala, Santa Rosa, CA (US)

(73) Assignee: Aryx Therapeutics, Los Altos Hills, CA (US)

( * ) Notice: Subject to any disclaimer, the term of this patent is extended or adjusted under 35 U.S.C. 154(b) by 0 days.

(21) Appl. No.: 10/273,702

(22) Filed: Oct. 18, 2002

(65) Prior Publication Data

US 2003/0078284 A1 Apr. 24, 2003

Related U.S. Application Data

(63) Continuation of application No. 09/841,749, filed on Apr. 24, 2001, now Pat. No. 6,469,064.
(60) Provisional application No. 60/199,343, filed on Apr. 24, 2000.

(51) Int. Cl.[7] .......................... A61K 31/24; C07C 229/00
(52) U.S. Cl. .......................................... 514/538; 560/35
(58) Field of Search ........................... 514/538; 560/35; 564/164

(56) References Cited

U.S. PATENT DOCUMENTS

| | | | |
|---|---|---|---|
| 4,085,225 A | 4/1978 | Welle et al. | |
| 5,686,447 A | 11/1997 | Shutske et al. | |
| 5,770,740 A | 6/1998 | Shutske et al. | |
| 6,469,064 B2 * | 10/2002 | Druzgala | 514/538 |

FOREIGN PATENT DOCUMENTS

| | | |
|---|---|---|
| GB | 1533063 A | 11/1978 |
| NL | 7610399 | 3/1978 |

* cited by examiner

*Primary Examiner*—Paul A. Zucker
(74) *Attorney, Agent, or Firm*—Saliwanchik, Lloyd & Saliwanchik

(57) ABSTRACT

The subject invention provides compounds which are easily metabolized by the metobolic drug detoxification systems. Particularly, fluvoxamine analogs which have been designed to include esters within the structure of the compounds are taught. Also provided are methods of treating depression and affective disorders, such as obsessive compulsive disorder. Pharmaceutical compositions of the fluvoxamine analogs are also taught.

8 Claims, No Drawings

MATERIALS AND METHODS FOR THE TREATMENT OF DEPRESSION

CROSS-REFERENCE TO RELATED APPLICATION

This application is a continuation of U.S. Ser. No. 09/841,749, filed Apr. 24, 2001; now U.S. Pat. No. 6,469,064 which claims priority from provisional patent application U.S. Ser. No. 60/199,343, filed Apr. 24, 2000.

BACKGROUND OF THE INVENTION

Major depression represents one of the most common mental illness, affecting between 5–10% of the population. The disease is characterized by extreme changes in mood which may also be associated with psychoses. It has generally been found that most antidepressant agents exert significant effects on the regulation of monoamine neurotransmitters, including serotonin.

A number of types of antidepressants have been developed in recent years. Many of these compounds regulate serotonin (5-hydroxytryptamine; 5-HT). Trazodone controls the actions of 5-HT while fluoxetine is a potent and selective inhibitor of 5-HT reuptake. 3-Chloroimipramine which inhibits both 5-HT and norepinephrine reuptake has been extensively used as an antidepressant in Europe and Canada. Other compounds which are of current interest or have been examined as antidepressants include fluvoxamine, citalopram, zimeldine, sertraline, bupropion and nomifensine. Fluvoxamine facilitates serotoninergic neurotransmission via potent and selective inhibition of serotonin reuptake into presynaptic neurons.

The serotonergic neural system of the brain have been shown to influence a variety of physiologic functions, and the compounds of the present invention are predicted to have the ability to treat in mammals, including humans, a variety of disorders associated with this neural system, such as eating disorders, depression, obsessive compulsive disorders, panic disorders, alcoholism, pain, memory deficits and anxiety. Other indications for antidepressants, such as fluvoxamine, include unipolar depression, dysthymia, bipolar depression, treatment-resistant depression, depression in the medically ill, panic disorder, obsessive-compulsive disorder, eating disorders, social phobia, and premenstrual dysphoric disorder.

The adverse effects occurring most frequently during treatment with selective serotonin reuptake inhibitors (SSRI(s)) such as fluvoxamine are gastrointestinal disturbances, such as, for example nausea, diarrhoea/loose stools, constipation, with an incidence of 6 to 37% (Drugs 43 (Suppl. 2), 1992). Nausea is the main adverse effect in terms of incidence. These adverse effects, although mild to moderate in severity, shy some patients away from treatment with SSRIs. The percentage of patients withdrawing because of nausea ranges from 3 to 8% of the patients. Moreover it has been frequently observed that after administration of SSRIs, patients suffer from dyspepsia. Fluvoxamine also causes a variety of other adverse effects including anorexia, dry mouth, headache, nervousness, skin rash, sleep problems, somnolence, liver toxicity, mania, increased urination, seizures, sweating increase, tremors, and Tourette's syndrome.

Drug toxicity which causes adverse effects is an important consideration in the treatment of individuals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the clinical knowledge of the patient, the disease and its history of progression, and any known adverse effects associated with a drug.

Drug elimination is the result of metabolic activity upon the drug and the subsequent excretion of the drug from the body. Metabolic activity can take place within the vascular supply and/or within cellular compartments or organs. The liver is a principal site of drug metabolism. The metabolic process can be broken down into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

BRIEF SUMMARY OF THE INVENTION

The subject invention provides materials and methods for the safe and effective inhibition of serotonin reuptake. In a preferred embodiment, the subject invention provides therapeutic compounds for the treatment of depression. The compounds of the subject invention can be used to treat at-risk populations, thereby bringing relief of symptoms, improving the quality of life, preventing acute and long-term complications, and treating accompanying disorders.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of treatment for depression.

In a further embodiment, the subject invention pertains to the breakdown products which are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

This invention is drawn to compounds which are more easily metabolized by the metabolic drug detoxification systems. This invention is also drawn to methods of treating disorders, such as obsessive compulsive disorder, depression, or disorders associated with serontonergic hypofunction. Specifically, this invention provides analogs of drugs which have been designed to be more susceptible to degradation by hydrolases, particularly serum and/or cytosolic esterases and methods of treatment comprising the administration of these analogs to individuals.

DETAILED DISCLOSURE OF THE INVENTION

The subject invention provides materials and methods for the treatment of depression and other disorders related to serotonin re uptake. Advantageously, the therapeutic compounds of the subject invention are stable in storage but have a relatively short half-life in the physiological environment; therefore, the compounds of the subject invention can be used with a lower incidence of side effects and toxicity.

In a preferred embodiment of the subject invention, therapeutic compounds are provided which are useful in the treatment of depression and which contain moiety, such as an ester group, which is susceptable to degradation by hydrolases, thereby breaking down the compound and facilitating its efficient removal from the treated individual. In a preferred embodiment, the therapeutic compounds are metabolized by the Phase I drug detoxification system.

A further aspect of the subject invention pertains to the breakdown products which are produced when the therapeutic compounds of the subject invention are acted upon by a hydrolase. The presence of these breakdown products in the urine or serum can be used to monitor the rate of clearance of the therapeutic compound from a patient.

Degradation of the compounds of the subject invention by enzymes such as hydrolases (esterases, peptidases, lipases, glycosidases, phosphateases, etc.) is particularly advantageous for drug metabolism because these enzymes are ubiquitously distributed and their activity is not dependent on age, gender, or disease state to the same extent as oxidative hepatic drug metabolism.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site which is convenient in the manufacturing process for the target drug. Additionally, the sensitivity of the ester linkage may be manipulated by the addition of side groups which hinder or promote the hydrolytic activity of the hydrolases responsible for cleaving the drug. Methods of adding such side groups, as well as the side groups themselves, are well known to the skilled artisan and can be readily carried out utilizing the guidance provided herein.

The subject invention further provides methods of treating disorders, such as depression comprising the administration of a therapeutically effective amount of esterified fluvoxamine analogs to an individual in need of treatment. Fluraxamine and various related compounds are described in, for example, U.S. Pat. No. 4,085,225 which is incorporated herein in its entirety by reference. Accordingly, the subject invention provides esterified fluvoxamine analogs and pharmaceutical compositions of these esterified compounds.

This invention is also drawn to methods of treating depression, disorders associated with serontonergic hypofunction, and affective disorders, such as obsessive compulsive disorder, comprising the administration of a therapeutically effective amount of the esterified fluvoxamine analog compounds to an individual in need of treatment. The invention is also applicable to other disorders associated with serotonin hypofunction (see U.S. Pat. Nos. 5,686,447 and 5,770,740 hereby incorporated by reference in their entireties).

Oxime ether compounds of the subject invention have the following structure:

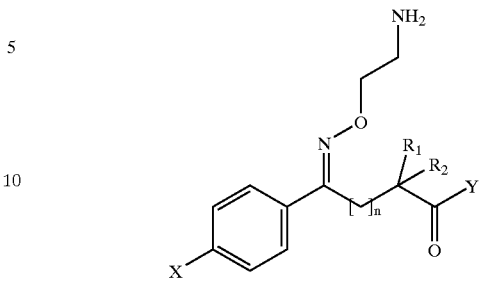

Pharmaceutically acceptable acids include fumarate, maleate, citrate, hydrochloride, phosphate, and gluconate. X is fluoro, chloro, iodo, trifluoromethyl, methoxy, cyano, nitro, amino, mono- or di-substituted amino, carboxamide, carboxylic acid, carboxylic ester, sulfonic acid, methyl sulfonate, or sulfonamide.

n is from 0 to 12, preferably from 0 to 6, and more preferably from 0 to 4, $R_1$ and $R_2$ are, independently, H, $C_{1-10}$ alkyl, or $R_1$ and $R_2$ are methylene groups that are part of a cyclic structure, such cyclic structure being, for example, cyclopropyl, cyclobutyl, cyclopentyl, or cyclohexyl. The cyclic structure can also be substituted with 1 to 4 alkyl groups.

Y can be $OR_3$, where $R_3$ is a linear or branched alkyl group having 1 to 12 carbon atoms, or $R_3$ is benzyl, substituted benzyl, aryl, heteroaryl, substituted aryl, or substituted heteraryl.

Y can also be $NR_4R_5$ where $R_4$ and $R_5$ are independently H, methyl, ethyl, or $R_4$ and $R_5$ are methylene groups that are part of a cyclohexyl ring. The cyclohexyl ring can in turn be substituted with 1 to 4 alkyl groups.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, 54$^{th}$ Ed., Medical Economics Company, Montvale, N.J., 2000).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be a rodent, for example a mouse or rat, pig, horse, rabbit, goat, pig, cow, cat, dog, or human. In a preferred embodiment, the individual is a human.

Following are examples which illustrate procedures for practicing the invention. These examples should not be construed as limiting. All percentages are by weight and all solvent mixture proportions are by volume unless otherwise noted.

An exemplary reaction scheme for the production of esterified fluvoxamine compounds, such as 5-methyl-5-oxo-4'-trifluoromethylvalerophenone O-(2-aminoethyl oxime, hydrochloride is provided below.

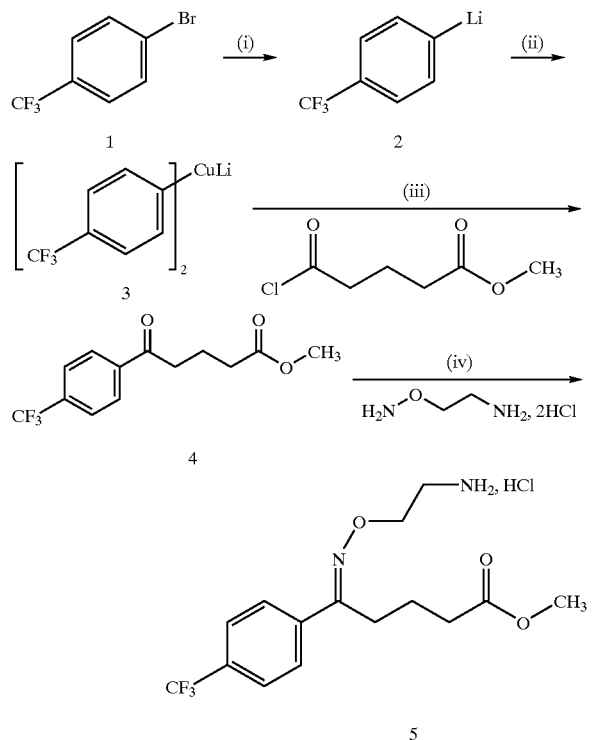

(i) 4-bromobenzotrifluoride 1 reacts with butyl lithium at −70° C. in anhydrous THF to give the lithium salt 2. (ii) The lithium salt reacts with copper(I) iodide to form the lithium diaryl cuprate complex 3 at −40° C. (iii) The complex 3 in turn reacts with methyl glutaryl chloride to form the valerophenone 4. (iv) Compound 4 forms an oxime with 2-aminooxyethylamine, dihydrochloride, in pyridine and absolute ethanol at reflux temperature to form the target compound 5.

The number of methylene groups between the terminal carboxyl and the oxime moiety can be controlled in step (iii). In the above described reaction scheme, the number of methylene groups is $(CH_2)_n$, where n is equal to 3. By using methyl succinyl chloride in step (iii) instead of methyl glutaryl chloride, then one obtains n=2. Similarly, by using methyl malonyl chloride, then n=1.

Modifications of the compounds disclosed herein can readily be made by those skilled in the art. Thus, analogs, and salts of the exemplified compounds are within the scope of the subject invention. With a knowledge of the compounds of the subject invention, and their structures, skilled chemists can use known procedures to synthesize these compounds from available substrates.

As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

It should be understood that the examples, reaction schemes, and embodiments described herein are for illustrative purposes only and that various modifications or changes in light thereof will be suggested to persons skilled in the art and are to be included within the spirit and purview of this application and the scope of the appended claims.

I claim:

1. A method for treating a disease state which can be improved by a serotonin reuptake inhibitor wherein said method comprises administering, to an individual in need of such treatment, a compound, or salt thereof, wherein said compound has the following structure:

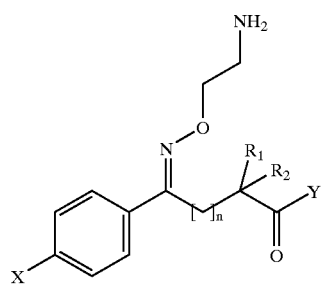

$R_1$ and $R_2$ are independently H, $C_{1-10}$ alkyl, or $R_1$ and $R_2$ are methylene groups that are part of a cyclic structure;

Y is $OR_3$, where $R_3$ is a linear or branched alkyl group having 1 to 12 carbon atoms, or $R_3$ is benzyl, substituted benzyl, aryl, heteroaryl, substituted aryl, or substituted heteraryl;

X is fluoro, chloro, iodo, trifluoromethyl, methoxy, cyano, nitro, amino, mono- or di-substituted amino, carboxamide, carboxylic acid, carboxylic ester, sulfonic acid, methyl sulfonate, or sulfonamide; and wherein said disease state is selected from the group consisting of depression, obsessive compulsive disorders and premature ejaculation.

2. The method, according to claim 1, wherein said disease state is depression.

3. The method, according to claim 1, wherein said individual is a human.

4. The method, according to claim 1, wherein X is CF3.

5. A pharmaceutical composition comprising a compound, or a salt thereof, wherein said compound has the following structure:

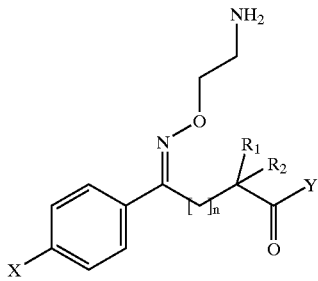

R₁ and R₂ are independently H, $C_{1-10}$ alkyl, or R₁ and R₂ are methylene groups that are part of a cyclic structure;

Y is OR₃, where R₃ is a linear or branched alkyl group having 1 to 12 carbon atoms, or R₃ is benzyl, substituted benzyl, aryl, heteroaryl, substituted aryl, or substituted heteraryl;

X is fluoro, chloro, iodo, trifluoromethyl, methoxy, cyano, nitro, amino, mono- or di-substituted amino, carboxamide, carboxylic acid, carboxylic ester, sulfonic acid, methyl sulfonate, or sulfonamide; and n is from 0 to 4 together with a pharmaceutical carrier.

6. The pharmaceutical composition, according to claim 5, wherein X is CF₃.

7. A compound, or salt thereof, wherein said compound has the following structure:

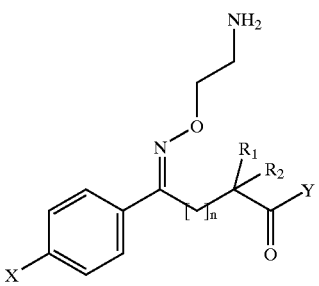

R₁ and R₂ are independently H, $C_{1-10}$ alkyl, or R₁ and R₂ are methylene groups that are part of a cyclic structure;

Y is OR₃, where R₃ is a linear or branched alkyl group having 1 to 12 carbon atoms, or R₃ is benzyl, substituted benzyl, aryl, heteroaryl, substituted aryl, or substituted heteraryl;

X is fluoro, chloro, iodo, trifluoromethyl, methoxy, cyano, nitro, amino, mono- or di-substituted amino, carboxamide, carboxylic acid, carboxylic ester, sulfonic acid, methyl sulfonate, or sulfonamide; and n is from 0 to 4 together with a pharmaceutical carrier.

8. The compound, according to claim 7, wherein X is CF₃.

* * * * *

UNITED STATES PATENT AND TRADEMARK OFFICE
CERTIFICATE OF CORRECTION

PATENT NO. : 6,809,116 B2
DATED : October 26, 2004
INVENTOR(S) : Pascal Druzgala It is certified that error appears in the above-identified patent and that said Letters Patent is hereby corrected as shown below:

Column 1,
Lines 30 and 31, "...scrotonin" should read -- serotonin --.

Column 6,
Lines 60 and 61, "fonic acid, methyl sulfonate, or sulfonamide; and wherein said disease state...ejaculation." should read -- fonic acid, methyl sulfonate, or sulfonamide; and
　　n is from 0 to 4
wherein said disease state ...ejaculation. --

Signed and Sealed this

Seventeenth Day of May, 2005

JON W. DUDAS
*Director of the United States Patent and Trademark Office*